United States Patent [19]

Frajdenrajch

[11] 4,310,305
[45] Jan. 12, 1982

[54] MECHANICAL DEVICE FOR HOLDING ELASTIC ARTICLES

[76] Inventor: Jacob Frajdenrajch, 9 Rue Croix Baragon, 13000 Toulouse, France

[21] Appl. No.: 962,642

[22] Filed: Nov. 21, 1978

[30] Foreign Application Priority Data

Nov. 25, 1977 [FR] France ............... 77 35616

[51] Int. Cl.³ .............................................. A61C 3/14
[52] U.S. Cl. ..................................... 433/4; 433/155; 433/159
[58] Field of Search ............... 32/63, 64, 66, 14 A, 32/14 D, 14 E; 81/302; 29/235, 268, 303, 305, 306, 304, 311, 312

[56] References Cited

U.S. PATENT DOCUMENTS 2,528,508 11/1950 Gabel ................................ 29/235
2,725,632 12/1955 Rabben ............................. 32/66

Primary Examiner—Robert Peshock
Attorney, Agent, or Firm—Sandler & Greenblum

[57] ABSTRACT

A mechanical device for holding elastic articles comprising a pair of circlips pliers having a set of primary jaws and a set of handles. The primary jaws are adapted to open when the handles are squeezed together. The pliers further comprise a set of secondary jaws, each of the secondary jaws being arranged on a corresponding primary jaw and being spaced from the primary jaws so as to hold the elastic articles.

14 Claims, 6 Drawing Figures

MECHANICAL DEVICE FOR HOLDING ELASTIC ARTICLES

The present invention relates to the techniques of odontologiastomatologia and more specially to orthodontic practice.

In the odontological speciality of orthodontics it is necessary to set a metallic ring or band around a tooth. The ring or band is provided with a bracket or tube allowing by means of a metallic arch or stem or by means of a fiber glass arch or stem, to transmit to the ring (and the tooth) the strength for coming to its place.

The proximity and even the contact of contiguous teeth which must be separated temporarily makes the operation difficult. For this operation one may use wire (such as brass wire) or natural silk threads or rubber ring or elastic separators such as "MAXIAN'S separators' made of an elastic rubber band provided on each extremity with a cylindrical bulges the separator having two bulges.

A thin band of this separator is then cut or a separator ready for use is employed. This separator or band is shaped and introduced between the two teeth.

To proceed with this operation the separator is held and stretched by the bulges between the thumb and the forefinger of the operator which set it in place.

By releasing the band of the separator, it reassumes its initial shape and section and separates the teeth.

This type of separator is easy to set in place between the anterior teeth or front teeth of the mouth but it is much more difficult to place this separator in the posterior area of the mouth when the practitioner has big fingers or when the mouth opening is narrow.

SUMMARY OF THE INVENTION

One of the main objects of the invention is to allow an easy placement of an elastic separator of this type without introduction of the fingers into the mouth.

The device according to the invention allows a better view of the mouth by the practitioner and a good retention of the band when the device is taken away.

Furthermore the device according to the invention allows the use of all types of elastic separators founded on the principle of MAXIAN'S type separator.

According to a first characteristic the invention concerns a mechanical device for holding elastic articles, able to be used particularly in orthodontic practice. The device includes a pair of circlips pliers whose jaws part when the handles are clenched, and is characterized by a first pair of jaws, called principal jaws, are associated with a second pair of jaws called secondary jaws. The second pair of jaws is separated by a space from the principal jaws in order to assume the holding of the elastic article.

According to a second feature the device includes bent jaws and the ends of the secondary jaws may be drawn toward the extremities of the principal jaws in translation by elastic means. The invention will be more clearly understood with reference to the description illustrated in the accompanying drawings

DESCRIPTION OF PREFERRED EMBODIMENTS

Figure 1:
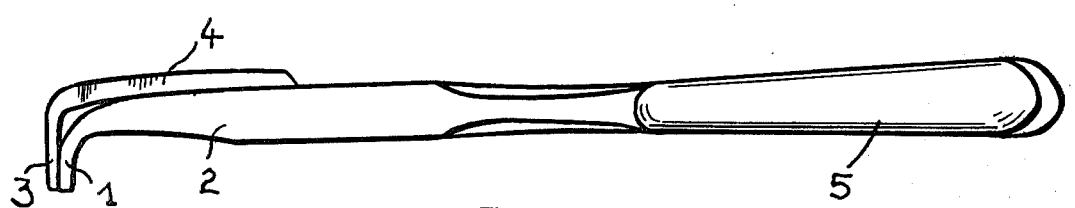
FIG. 1 is a side view of one embodiment of the invention.
Figure 2:
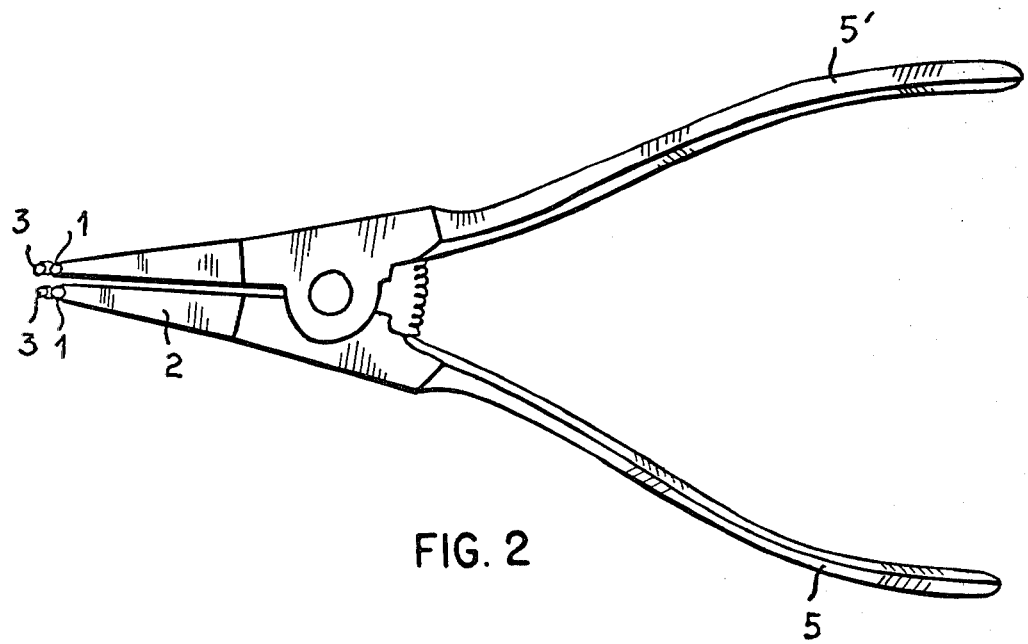
FIG. 2 is a bottom view of the embodiment shown in FIG. 1.

A first example of the invention is shown in FIGS. 1 and 2 showing a simple embodiment.

The device of the invention comprises a pair of pliers with a pair of principal jaws each having a bent extremity 1 and a linear portion 2, and with a pair of secondary jaws each having a bent extremity 3 and a linear portion 4.

In this embodiment the secondary jaws are fixed relative to the principal jaws. The junction is made by soldering or other means and the secondary jaws are arranged at a short distance from the principal jaws in order to allow the insertion between the bent part of the principal jaws and the bent part of the secondary jaws of the elastic separator's band. Each of the separator's bulges are respectively located on each side of the plier made by the secondary 3 and principal jaws 1.

The separator being so disposed, the handles 5 et 5' of the pliers are squeezed which results in a stretching of the elastic separator's band whose section is reduced to allow the placement of the elastic separator between two teeth.

Figure 3:
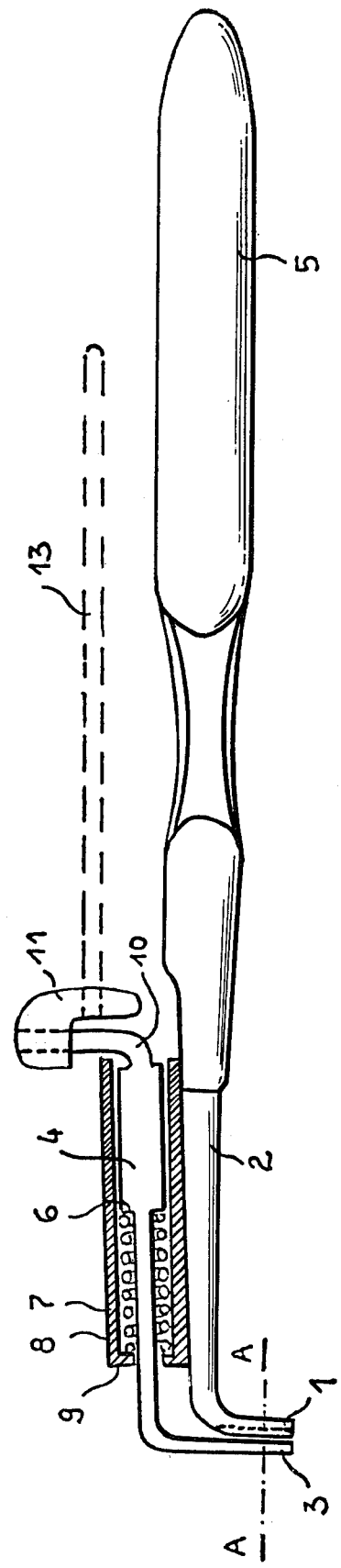
FIG. 3 is a modified embodiment of the invention.

When the band is set in place the handles 5, 5'of the pliers are opened to allow the band to recover its initial section and to push or part the two contiguous teeth. The practitioner then takes out the pliers. During this operation the practitioner holds the edges of the band with the fingers. FIG. 3 illustrates an improved embodiment of the invention in which the bent extremity of each secondary jaw may be kept near the bent extremity of the principal jaw by elastic means.

In this embodiment the linear portion of the secondary jaw is guided by and linearly movable in a linear bore of a tube 7 fixed on the axis of the linear portion 2 of the principal jaw. The tube is fixed on the principal jaw by soldering or some other way. The bore may likewise be arranged in the linear portion of the principal jaw.

The elastic or biasing means causing the closure of the secondary jaw is a spring 8. One end of the spring leans on a circular shoulder 9 of the bore and the other end leans on an abutment 6 of the linear portion 4 of the secondary jaw.

It is possible to replace the spring by a plastic and elastic hollowed fillet made of synthetic material, which surrounds 8 the linear portion 4 of the secondary jaw.

Any other devices may be used to replace the spring. The cross-section of the bent portion 3 may be square, rectangular or circular.

Figure 4:
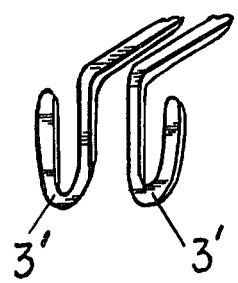
FIG. 4 illustrates loop-shaped bent portions.

In this event it could be desirable to bend the portion 3' in a loop shape which results in a better prehension of the elastic separator as shown in FIG. 4 in which the loop is illustrated in front position.

Figure 5:
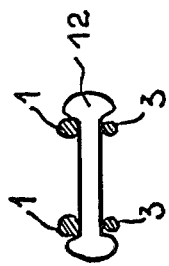
FIG. 5 is a view along line A—A of FIG. 3.

In this embodiment the rear portion 10 of the linear portion 4 of each secondary jaw is bent upright and may be joined with the other secondary jaws by means of a junction piece 11. This feature permits the practitioner to insert the band 12 between the bent extremities 1 of the pair of principal jaws and the bent extremities 3 of the secondary jaws as shown in FIG. 5 with band 12 shown in cross-section along the line AA' of FIG. 3.

In this operation the practitioner leans or presses against the junction piece 11 in order to part the secondary jaws from the principal jaw.

The separator being ready between the jaws, the practitioner may set it in place between two contiguous teeth by squeezing the handles 5 and 5' of the plier.

After releasing the handles the practitioner takes over the plier by leaning on the junction piece 11 in order to part the secondary jaws from the principal jaws.

Figure 6:
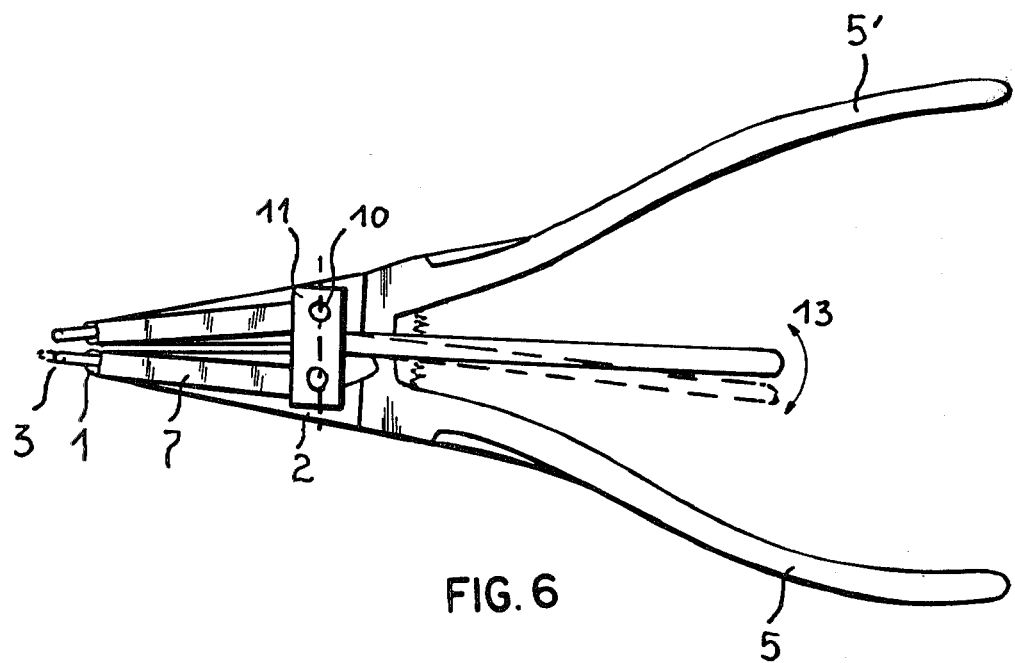
FIG. 6 is a top view of the device illustrated in FIG. 3.

According to a preferred embodiment a drive arm 13 (shown in dashed lines in FIG. 3 and in solid lines in FIG. 6) is set in the junction piece by one end, the other end of the drive arm being free.

The drive arm is located eventually in an unwedge plane in comparison to the plane of the handle 5 and 5' of the plier. This device is operated by means of the drive arm: by finger's push on the drive arm towards one of the plier's handles removal of the secondary jaw located on the same side as the handles results.

The positioning of the separator on the device is facilitated by the introduction one after the other of each side or end of the separator between each pair of jaws, (principal jaw and secondary jaw).

The junction piece may have an articulation allowing the pratitioner to achieve the simultaneous removal of the two secondary jaws by a single downward or upward push, the axis of the articulation being parallel to the plane of the handles. Thus when the practitioner wants to take the separator off of the device according to the invention he need only push with one finger on the drive arm.

According to a supplemental feature of the invention the device may have a flexion spring whose, one end is fixed on the plier's axis and whose other end leans on the drive arm in order to keep the drive arm in an upright position.

In all the examples described, most effective translational guidance of the secondary jaws may be obtained with respect to the primary jaws by giving the linear portion of the secondary jaw a square cross-section, an identical cross-section being given to the bore in which the linear portion of the secondary jaw moves.

This feature of the invention avoids, when the jaws are opened by squeezing the handles 5 and 5'one towards the other, an untimely rotation of the secondary jaws in their bores. This rotation results in the secondary jaws not being exactly parallel with the primary jaws.

According to another feature of the invention each device previously described may have, on the section of the bent end or extremity of each primary jaw, a notch shaped to receive and take the exact shape of the section of the secondary jaws.

By this means when the secondary jaw is pulled towards the principal jaw by elastic means it fits into the back of the notch allowing a stronger pinching and a better grip of the elastic article.

Although the present invention has been described with respect to specific examples it has been clear that this description is made by way of example without any limitation of the scope of the invention.

While the device according to the invention finds particular application in orthodontic practice, it can also be used in surgery or in mechanical application and more generally in all parts of industry where it is necessary to hold elastic pieces such as watch-making or jewelry making.

I claim:

1. A mechanical device for holding elastic articles, comprising a pair of circlips pliers having a set of primary jaws and a set of handles, said primary jaws being adapted to open when said handles are squeezed together, said pliers further comprising a set of secondary jaws, each of said secondary jaws being arranged on a corresponding primary jaw, said secondary jaws being spaced from said primary jaws so as to hold said elastic articles and wherein said secondary jaws are adapted to move with respect to said primary jaws, and further wherein each of said primary and secondary jaws is bent and said bent portions of each of said primary jaws comprises a notch, said notch being adapted to receive the corresponding secondary jaw such that said secondary jaw fits within said notch when the bent portions of said secondary jaws are pulled towards said bent portions of said primary jaws.

2. A mechanical device for holding elastic articles, comprising a pair of circlips pliers having a set of primary jaws and a set of handles, said primary jaws being adapted to open when said handles are squeezed together, said pliers further comprising a set of secondary jaws, each of said secondary jars being arranged on a corresponding primary jaw, said secondary jaws being spaced from said primary jaw so as to hold said elastic articles and wherein said secondary jaws are biased against said primary jaws by means of biasing means.

3. The mechanical device as defined by claim 2, wherein each of said principal jaws is provided with a linear portion having a tube mounted thereon and each of said secondary jaws comprises a linear portion arranged within one of said tubes.

4. The mechanical device as defined by claim 3 wherein said elastic means comprises a spring arranged around each of said linear portions of said secondary jaws and within each of said tubes on said primary jaws, said springs being contained within said tubes between a circular shoulder on one end of said tubes and an abutment on each of said secondary jaws.

5. The mechanical device as defined by claim 4 further comprising a junction piece forming a junction between each of said secondary jaws.

6. The mechanical device as defined by claim 5 wherein said junction piece is adapted to permit either simultaneous or sequential movement of each of said secondary jaws.

7. The mechanical device as defined by claim 6 further comprising a drive arm connected to said junction piece at one end of said drive arm, said drive arm being arranged between each of said handles and ending in a free end located in a plane offset from the plane of said set of handles.

8. The mechanical device as defined by claim 7 wherein said junction piece is articulated onto said device and wherein said drive arm and said junction piece are adapted to move both of said secondary jaws simultaneously as a result of said drive arm being pushed downwardly towards the plane of said handles.

9. The mechanical device as defined by claim 8 further comprising a spring arranged between said pliers and said drive arm so as to maintain said drive arm in an upright position.

10. The mechanical device as defined by claim 2 wherein each of said secondary jaws is arranged within a bore in each of said primary jaws.

11. A mechanical device for holding elastic articles, comprising a pair of circlips pliers having a set of primary jaws and a set of handles, said primary jaws being adapted to open when said handles are squeezed together, said pliers further comprising a set of secondary jaws being arranged on a corresponding primary jaw, each of said secondary jaws and adapted to move relative to said primary jaws so as to hold said elastic articles, and wherein each of said secondary jaws is bent at one end thereof and has a circular cross section and further wherein each of said ends of said secondary jaws is doubled over into a loop.

12. A mechanical device for holding elastic articles, comprising a pair of circlips pliers having a set of primary jaws and a set of handles, said primary jaws being adapted to open when said handles are squeezed together, said pliers further comprising a set of secondary jaws being arranged on a corresponding primary jaw, each of said secondary jaws being spaced from and movable with respect to said primary jaws so as to hold said elastic articles, and wherein the ends of each of said secondary jaws is bent at one end thereof, and said bent end has a square or rectangular cross-section.

13. A mechanical device for holding elastic articles, comprising a pair of circlips pliers having a set of primary jaws and a set of handles, said primary jaws being adapted to open when said handles are squeezed together, said pliers further comprising a set of secondary jaws, each of said secondary jaws being arranged on a corresponding primary jaw, said secondary jaws being spaced from said primary jaws so as to hold said elastic articles, and wherein said secondary jaws are adapted to move with respect to said primary jaws, and wherein a linear portion of each of said secondary jaws is arranged within a tube attached to a linear portion of said primary jaws each of said tubes acting to guide one of said secondary jaws, and further wherein the cross-section of each of said linear portions of said secondary jaws is square and the cross-section of said tube is square.

14. The mechanical device as defined wherein each of said ends of said secondary jaws is doubled over into a loop.

* * * * *

UNITED STATES PATENT AND TRADEMARK OFFICE
CERTIFICATE OF CORRECTION

PATENT NO. : 4,310,305

DATED : January 12, 1982

INVENTOR(S) : Jacob FRAJDENRAJCH

It is certified that error appears in the above—identified patent and that said Letters Patent is hereby corrected as shown below:

```
Column 1, line 19, " ' " should be --"--; and
          line 20, "bulges" should be --bulge,--.
Column 2, line 58, "3'" should be --3--.
Column 3, line 19, "handles" should be --handle--; and
          line 33, "spring whose," should be --spring,
whose--.
```

Signed and Sealed this

Eleventh Day of May 1982

[SEAL]

Attest:

Attesting Officer

GERALD J. MOSSINGHOFF

Commissioner of Patents and Trademarks